(12) United States Patent  
Grundei

(10) Patent No.: US 7,004,975 B2
(45) Date of Patent: Feb. 28, 2006

(54) COATED JOINT ENDOPROSTHESIS

(75) Inventor: Hans Grundei, Lübeck (DE)

(73) Assignee: ESKA Implants GmbH & Co., Lübeck (DE)

(*) Notice: Subject to any disclaimer, the term of this patent is extended or adjusted under 35 U.S.C. 154(b) by 0 days.

(21) Appl. No.: 10/983,220

(22) Filed: Nov. 5, 2004

(65) Prior Publication Data

US 2005/0102035 A1 May 12, 2005

(30) Foreign Application Priority Data

Nov. 7, 2003 (EP) .................................. 03025541

(51) Int. Cl.
*A61F 2/28* (2006.01)
*B32B 15/04* (2006.01)

(52) U.S. Cl. ................... 623/23.56; 623/23.36; 623/23.57; 623/18.11; 428/472

(58) Field of Classification Search ............. 623/23.56, 623/23.36, 18.11
See application file for complete search history.

(56) References Cited

U.S. PATENT DOCUMENTS

| 3,465,424 A | * | 9/1969 | Deringer .................... 29/527.2 |
| 4,605,415 A | * | 8/1986 | Richez ........................ 424/422 |
| 4,643,982 A | * | 2/1987 | Kasuga et al. ................. 501/8 |
| 4,820,660 A | * | 4/1989 | Mohri et al. .................... 501/8 |
| 4,960,733 A | * | 10/1990 | Kasuga et al. ................ 501/10 |
| 5,232,878 A | * | 8/1993 | Kasuga et al. ................ 501/10 |
| 5,282,869 A | * | 2/1994 | Miyajima et al. ......... 623/20.27 |

FOREIGN PATENT DOCUMENTS

| CH | 681 423 A5 | 3/1993 |
| DE | 43 17 448 A1 | 11/1994 |
| GB | 1 451 283 A | 9/1976 |

* cited by examiner

Primary Examiner—David J. Isabella
(74) Attorney, Agent, or Firm—Akin Gump Strauss Hauer & Feld, LLP

(57) ABSTRACT

Joint endoprostheses are provides which respectively have a joint part with a metallic core, wherein the metallic core is coated, in regions that roll and/or slide on another joint part during execution of the joint function, with a glass-ceramic composite mixture. In one embodiment, the glass-ceramic has the following composition with approximate amounts in wt. %:

| Component | Amount (wt %) |
|---|---|
| $SiO_2$ | 45–50% |
| $Al_2O_3$ | 15–20% |
| $ZrO_2$ | 8–12% |
| $K_2O$ | 0–8% |
| $Na_2O$ | 0–7.5% |
| $CaO$ | 0–2.5% |
| $TiO_2$ | 0–1.5% | and furthermore a residual amount of up to about 12.5% of $MnO_2$ and/or $Fe_2O_3$ and/or $Co_2O_3$.

15 Claims, 2 Drawing Sheets

COATED JOINT ENDOPROSTHESIS

BACKGROUND OF THE INVENTION

The invention relates to a joint endoprosthesis which has a joint part with a metallic core, which at least in regions rolls and/or slides on another joint part during execution of the joint function.

Typical examples of such a joint endoprosthesis are an artificial knee joint, a shoulder joint, and above all an artificial hip joint.

In this field various pairings of materials have been known for a long time, for example a metallic joint ball with a sliding partner in the form of an inlay of polyethylene in a pelvic hip socket (acetabulum), and likewise a hard ceramic joint ball with a hard ceramic or composite ceramic insert in an acetabulum.

Now as before, the abrasion phenomena in one of the sliding partners are problematic. Admittedly these are small, but measurable, which as a rule require a change of at least one joint part after a few years. This is not only a heavy burden on the patient, but also represents a considerable cost factor.

BRIEF SUMMARY OF THE INVENTION

Accordingly, the object of the present invention is to provide a joint endoprosthesis of the kind mentioned at the outset, which is stable for a long time and resistant to abrasion and moreover has a high strength of the joint components. Furthermore, a pairing of joint parts is to be given which has these advantageous properties.

This object is achieved by a joint endoprosthesis having a metallic core coated with any of three different glass-ceramic composite mixtures as set forth below.

All three embodiments provide a joint endoprosthesis which has a joint part with a metallic core, wherein the metallic core is coated with various compositions of a glass-ceramic composite mixture in regions which roll or slide on another joint part during execution of a joint function.

BRIEF DESCRIPTION OF THE SEVERAL VIEWS OF THE DRAWINGS

The foregoing summary, as well as the following detailed description of the invention, will be understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
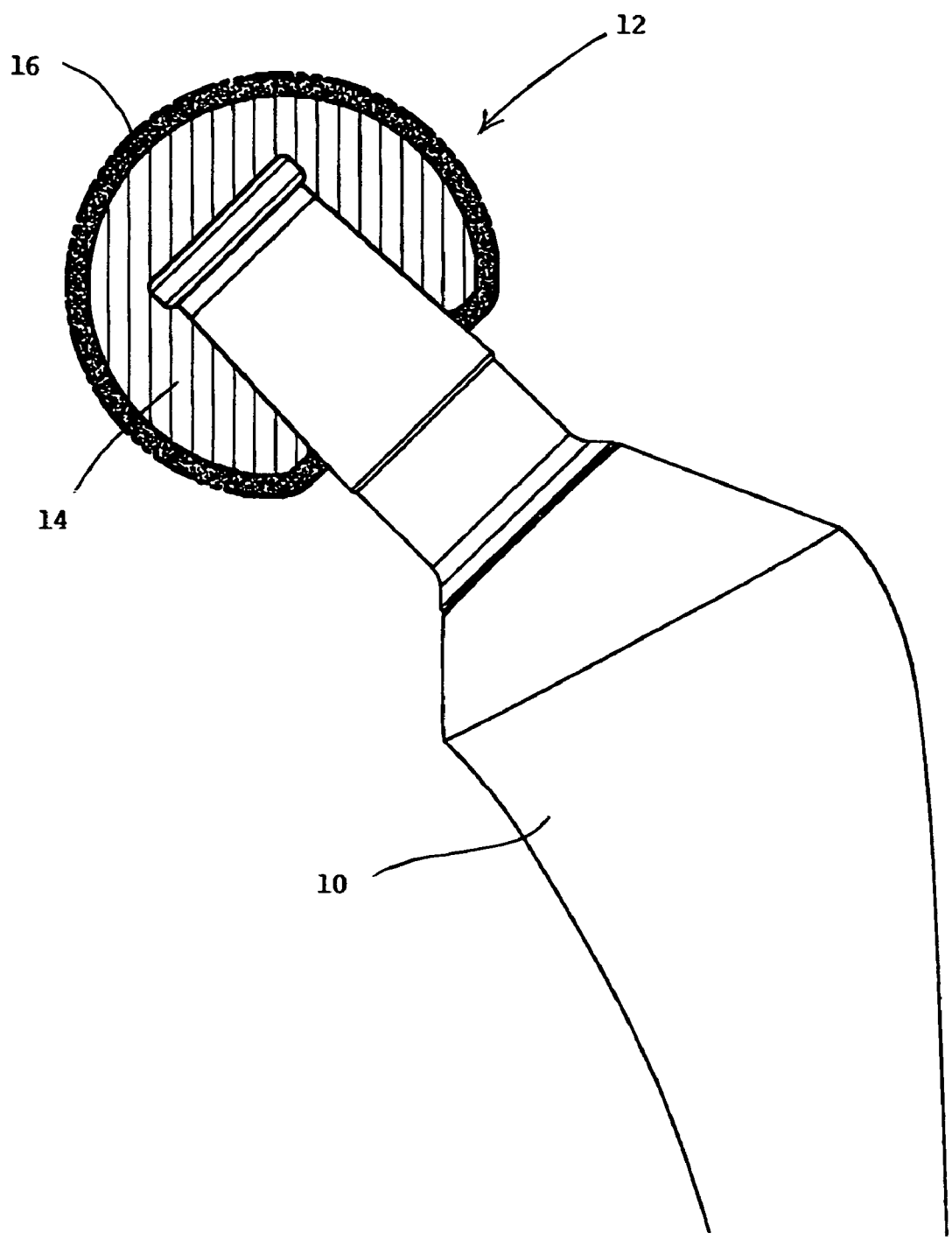
FIG. 1 is a schematic diagram, partially in section, showing an artificial hip shaft with a ball joint having a coating according to an embodiment of the invention.

According to a first embodiment, a composition is proposed, which is set forth below with the components in the following approximate amounts:

| Component | Amount (wt %) |
|---|---|
| $SiO_2$ | 45–50% |
| $Al_2O_3$ | 15–20% |
| $ZrO_2$ | 8–12% |
| $K_2O$ | 0–8% |
| $Na_2O$ | 0–7.5% |
| CaO | 0–2.5% |
| $TiO_2$ | 0–1.5% | and furthermore a residual amount of up to about 12.5% of $MnO_2$ and/or $Fe_2O_3$ and/or $Co_2O_3$.

The greatest portion in this composition is the glass portion $SiO_2$; by whose use the adhesion to the metallic base stands in the forefront. The components $Al_2O_3$ and $ZrO_2$ substantially influence the abrasion properties.

This composition of the glass ceramic is the hardest of the three embodiments. It is designated as a so-called bionic system, since it makes it possible for the other joint part, likewise with a metallic core, to be coated with a glass-ceramic composite mixture of the same composition. Lifetimes of 15–20 years are expected for the joint prosthesis bearing the described glass-ceramic composition of this embodiment.

According to a second embodiment, the following composition of glass-ceramic is proposed with the components in the following approximate amounts:

| Component | Amount (wt %) |
|---|---|
| $SiO_2$ | 35–55% |
| $Al_2O_3$ | 15–25% |
| $TiO_2$ | 10–14% |
| $Na_2O$ | 0–7.5% |
| $K_2O$ | 0–7% |
| $ZrO_2$ | 1–5% |
| CaO | 0–0.5% | and furthermore a residual amount of up to about 24% of $MnO_2$ and/or $Fe_2O_3$ and/or $Co_2O_3$ and/or CuO.

This system differs from the first embodiment, firstly in that the coating is somewhat softer than the first-named one. A decisive difference, however, is the substantially higher admixture of $TiO_2$. Consequently, an admittedly small, but unavoidable abrasion is tolerable by the body. This system is therefore also designated as anti-allergic. The lifetimes of a joint endoprosthesis equipped therewith may be found to be somewhat smaller than for the first joint endoprosthesis. Also, this system of this glass-ceramic composite mixture is so hard that the other joint part, likewise with a metallic core, can also be coated with the glass-ceramic composite mixture of the same composition as the first joint part.

According to the third embodiment, the first joint part is coated with a glass-ceramic of the following composition with the components present in the indicated approximate amounts:

| Component | Amount (wt %) |
|---|---|
| $SiO_2$ | 50–60% |
| $Al_2O_3$ | 5–10% |
| $ZrO_2$ | 5–10% |

-continued

| Component | Amount (wt %) |
|---|---|
| $Na_2O$ | 0–8% |
| CaO | 0–6% |
| $TiO_2$ | 3–5% |
| $K_2O$ | 0–2% |
| $Sb_2O_3$ | 0–0.5% | and furthermore a residual amount of up to about 20.5% of $MnO_2$ and/or $Fe_2O_3$ and/or $Co_2O_3$ and/or CuO and/or $CeO_2$.

This alternative makes available the softest material relative to the two other alternatives. Lifetimes of up to 15 years are likewise expected. Because of the relative softness of the material, it is preferably provided that the other joint part, on which the first joint part rolls and/or slides, has a sliding partner made of a ceramic, which is harder than the glass-ceramic composite mixture of the abovementioned composition. In this case, a composite ceramic is particularly preferred for the sliding partner, which is known, for example, from European Patent EP 0 502 082 C. Alternatively, a sliding partner made of polyethylene can be used for this purpose in the second joint part. The thus constructed joint endoprosthesis may be designated as the standard endoprosthesis, which is implanted into the average patient. Likewise, it has a longer lifetime than the known joint endoprostheses made with the pairings of metal against metal, metal against polyethylene, ceramic against polyethylene, etc., with a strength of the components which is clearly higher than with ceramic components in particular.

It is particularly preferred if the metallic cores of the joint parts comprise a cobalt-chromium-molybdenum alloy. Namely, it has been found that the adhesion strengths of the coatings to this metal are extremely high, so that damage to the coating, for example spalling, is highly improbable.

In all of the embodiments it is preferred that the thickness of the coating be about 200 μm to 600 μm. With an average abrasion of about 5 μm to 8 μm per year, extremely long lifetimes result, which are difficult to attain with material pairings according to the prior art.

The glass ceramic composite mixtures for forming the coatings of the invention are prepared by mixing the components of the composition, i.e., the various oxides which form the coating. The method of mixing is not critical and may be carried out by a variety of methods, which are known in the art per se, for forming glass ceramic coatings. Preferably, the oxide components in the form of powders or other fine particulates are mixed in a suitable binder, vehicle or carrier to form a slurry of the oxide particles.

The slurry may then be applied to the joint part or parts to be coated, for example by spraying the slurry onto the joint part or by dipping or immersing the joint part in the slurry. Next the coating is dried, for example by heating to evaporate the vehicle or carrier. Finally, the coated surface is further heated to fire the mixed oxide coating, so that the oxide particles are baked or sintered together on the surface of the joint part or the binder is cured, for example, depending on the particular method selected to set the coating to form a glass ceramic composite and adhere the composite to the surface and to each other.

Figure 2:
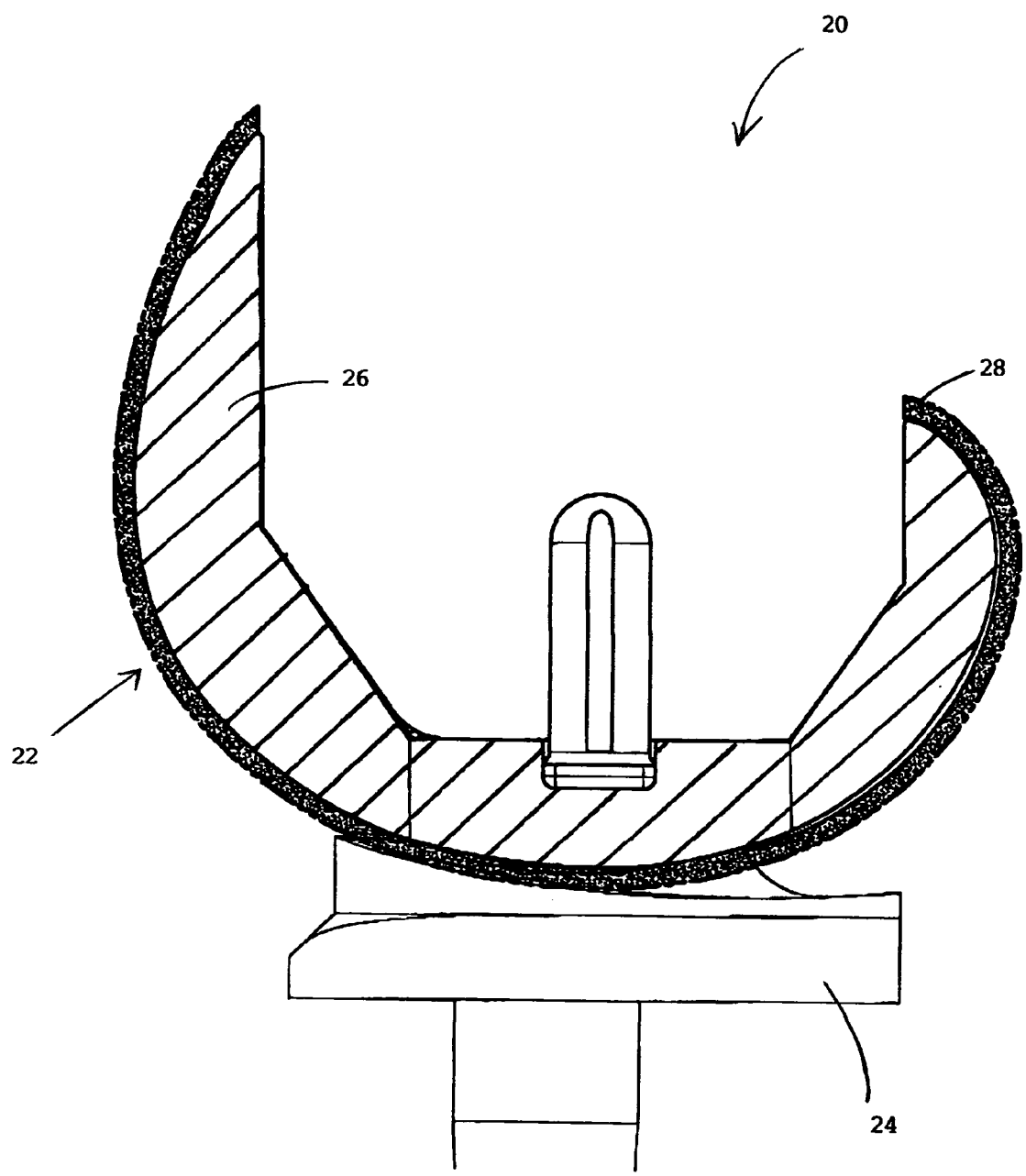
FIG. 2 is a schematic diagram, partially in section, showing a knee joint endoprosthesis having a coating according to an embodiment of the invention on the gliding member of the knee joint prosthesis.

Examples of uses of the coatings of the invention are shown in the drawings. In FIG. 1 an artificial hip shaft 10 is shown with a ball joint 12 for insertion into a hip socket (not shown). The ball joint 12 is formed of a metallic core 14, which is coated with a glass ceramic coating 16 according to the invention. In FIG. 2 a knee joint endoprosthesis 20 is shown comprising a gliding part 22 which rolls and/or slides on a mating part 24. The gliding part 22 is formed of a metallic core 26, which is coated with a glass ceramic coating 28 according to the invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A joint endoprosthesis, comprising a first joint part having a metallic core, wherein the metallic core is coated, in regions that roll and/or slide on a second joint part during execution of a joint function, with a glass-ceramic composite mixture having the following composition in approximate amounts indicated (in wt. %):

| Component | Amount (wt %) |
|---|---|
| $SiO_2$ | 45–50% |
| $Al_2O_3$ | 15–20% |
| $ZrO_2$ | 8–12% |
| $K_2O$ | 0–8% |
| $Na_2O$ | 0–7.5% |
| CaO | 0–2.5% |
| $TiO_2$ | 0–1.5% | and furthermore a residual amount of up to about 12.5% of an oxide selected from the group consisting of $MnO_2$, $Fe_2O_3$, $Co_2O_3$ and mixture thereof.

2. A joint endoprosthesis, comprising a first joint part having a metallic core, wherein the metallic core is coated, in regions that roll and/or slide on a second joint part during execution of a joint function, with a glass-ceramic composite mixture having the following composition in approximate amounts indicated (in wt. %):

| Component | Amount (wt %) |
|---|---|
| $SiO_2$ | 35–55% |
| $Al_2O_3$ | 15–25% |
| $TiO_2$ | 10–14% |
| $Na_2O$ | 0–7.5% |
| $K_2O$ | 0–7% |
| $ZrO_2$ | 1–5% |
| CaO | 0–0.5% | and furthermore a residual amount of up to about 24% of and oxide selected from the group consisting of $MnO_2$, $Fe_2O_3$, $Co_2O_3$, CuO, and mixtures thereof.

3. A joint endoprosthesis, comprising a first joint part having a metallic core, wherein the metallic core is coated, in regions that roll and/or slide on a second joint part during execution of a joint function, with a glass-ceramic composite mixture having the following composition in approximate amounts indicated (in wt. %):

| Component | Amount (wt %) |
|---|---|
| $SiO_2$ | 50–60% |
| $Al_2O_3$ | 5–10% |

-continued

| Component | Amount (wt %) |
|---|---|
| $ZrO_2$ | 5–10% |
| $Na_2O$ | 0–8% |
| CaO | 0–6% |
| $TiO_2$ | 3–5% |
| $K_2O$ | 0–2% |
| $Sb_2O_3$ | 0–0.5% | and furthermore a residual amount of up to about 20.5% of and oxide selected from the group consisting of $MnO_2$, $Fe_2O_3$, $Co_2O_3$, CuO, $CeO_2$, and mixtures thereof.

4. The joint endoprosthesis according to claim 1, wherein the coating has a thickness of about 200 to 600 μm.

5. The joint endoprosthesis according to claim 2, wherein the coating has a thickness of about 200 to 600 μm.

6. The joint endoprosthesis according to claim 3, wherein the coating has a thickness of about 200 to 600 μm.

7. The joint endoprosthesis according to claim 1, wherein the second joint part also has a metallic core which is coated with a glass-ceramic composite mixture of the same composition as the first joint part.

8. The joint endoprosthesis according to claim 2, wherein the second joint part also has a metallic core which is coated with a glass-ceramic composite mixture of the same composition as the first joint part.

9. The joint endoprosthesis according to claim 3, wherein the second joint part has a sliding partner comprising a ceramic.

10. The joint endoprosthesis according to claim 3, wherein the second joint part has a sliding partner comprising polyethylene.

11. The joint endoprosthesis according to claim 1, wherein the metallic core comprises a cobalt-chromium-molybdenum alloy.

12. The joint endoprosthesis according to claim 2, wherein the metallic core comprises a cobalt-chromium-molybdenum alloy.

13. The joint endoprosthesis according to claim 3, wherein the metallic core comprises a cobalt-chromium-molybdenum alloy.

14. The joint endoprosthesis according to claim 7, wherein the metallic core of the second joint part comprises a cobalt-chromium-molybdenum alloy.

15. The joint endoprosthesis according to claim 8, wherein the metallic core of the second joint part comprises a cobalt-chromium-molybdenum alloy.

* * * * *